(12) United States Patent
Gandhi et al.

(10) Patent No.: US 7,497,994 B2
(45) Date of Patent: *Mar. 3, 2009

(54) MICROFLUIDIC DEVICES AND SYSTEMS INCORPORATING COVER LAYERS

(76) Inventors: Khushroo Gandhi, 321 W. Meadows Dr., Palo Alto, CA (US) 94306; Gilbert T. Tong, 4442 Pomponi St., Union City, CA (US) 94587

( * ) Notice: Subject to any disclaimer, the term of this patent is extended or adjusted under 35 U.S.C. 154(b) by 1042 days.

This patent is subject to a terminal disclaimer.

(21) Appl. No.: 10/792,020

(22) Filed: Mar. 3, 2004

(65) Prior Publication Data
US 2004/0228770 A1 Nov. 18, 2004

Related U.S. Application Data

(63) Continuation-in-part of application No. 09/544,711, filed on Apr. 6, 2000, now Pat. No. 6,756,019, which is a continuation-in-part of application No. 09/028,965, filed on Feb. 24, 1998, now Pat. No. 6,251,343.

(51) Int. Cl.
*B01L 3/02* (2006.01)
(52) U.S. Cl. .................. 422/100; 422/68.1; 422/99; 422/103; 436/174; 436/179; 436/180; 435/288.3
(58) Field of Classification Search .............. 422/50, 422/68.1, 99–100, 103; 436/174, 179, 180; 435/288.3
See application file for complete search history.

(56) References Cited

U.S. PATENT DOCUMENTS 3,785,928 A 1/1974 Kessler (Continued)

FOREIGN PATENT DOCUMENTS

WO WO 96/04547 2/1996

(Continued)

OTHER PUBLICATIONS

Dasgupta, P.K. et al., "Electroosmosis: A Reliable Fluid Propulsion System for Flow Injection Analysis," *Anal. Chem.*(1994) 66:1792-1798.

(Continued)

*Primary Examiner*—Jill Warden
*Assistant Examiner*—Jyoti Nagpaul
(74) *Attorney, Agent, or Firm*—Cardinal Law Group

(57) ABSTRACT

The present invention provides microfluidic devices that comprise a body structure comprising at least a first microscale channel network disposed therein. The body structure has a plurality of ports or wells disposed in the body structure, where each port is in fluid communication with one or more channels in the first channel network. The devices also include a cover layer comprising a plurality of apertures disposed through the cover layer. The cover layer is mated with the body structure whereby each of the apertures is aligned with a separate one of the plurality of ports. First and second rings are preferentially disposed between the cover layer and the body structure and located circumferentially around each of the apertures of the cover layer. An annular groove is also preferentially disposed between the ring structures to help further minimize the leakage of adhesive or other bonding material into the ports or wells of the device when the cover layer is mated to the body structure.

14 Claims, 6 Drawing Sheets

U.S. PATENT DOCUMENTS

| | | |
|---|---|---|
| 3,939,623 A | 2/1976 | Shine et al. |
| 4,038,149 A | 7/1977 | Liner et al. |
| 4,252,132 A | 2/1981 | Kuntz |
| 4,390,403 A | 6/1983 | Batchelder |
| 4,493,815 A | 1/1985 | Fernwood et al. |
| 4,908,112 A | 3/1990 | Pace |
| 5,100,627 A | 3/1992 | Buican et al. |
| 5,107,987 A | 4/1992 | Palazzolo et al. |
| 5,126,022 A | 6/1992 | Soane et al. |
| 5,156,285 A | 10/1992 | Zogg et al. |
| 5,160,704 A | 11/1992 | Schluter |
| 5,180,480 A | 1/1993 | Manz |
| 5,296,114 A | 3/1994 | Manz |
| 5,296,375 A | 3/1994 | Kricka et al. |
| 5,304,487 A | 4/1994 | Wilding et al. |
| 5,427,946 A | 6/1995 | Kricka et al. |
| 5,484,731 A | 1/1996 | Stevens |
| 5,486,335 A | 1/1996 | Wilding et al. |
| 5,498,392 A | 3/1996 | Wilding et al. |
| 5,571,410 A | 11/1996 | Swedberg et al. |
| 5,585,069 A | 12/1996 | Zanzucchi et al. |
| 5,593,838 A | 1/1997 | Zanzucchi et al. |
| 5,599,432 A | 2/1997 | Manz et al. |
| 5,603,351 A | 2/1997 | Cherukuri et al. |
| 5,635,358 A | 6/1997 | Wilding et al. |
| 5,635,403 A | 6/1997 | Bailey |
| 5,637,469 A | 6/1997 | Wilding et al. |
| 5,640,995 A | 6/1997 | Packard et al. |
| 5,699,157 A | 12/1997 | Parce |
| 5,726,026 A | 3/1998 | Wilding et al. |
| 5,779,868 A | 7/1998 | Parce et al. |
| 5,800,690 A | 9/1998 | Chow et al. |
| 5,842,787 A | 12/1998 | Kopf-Sill et al. |
| 5,852,495 A | 12/1998 | Parce |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,958,343 A | 9/1999 | Astle |
| 6,251,343 B1 * | 6/2001 | Dubrow et al. ............... 422/102 |
| 6,756,019 B1 * | 6/2004 | Dubrow et al. ............... 422/102 |

FOREIGN PATENT DOCUMENTS

| | | |
|---|---|---|
| WO | WO 97/02357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56505 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/31495 | 6/1999 |
| WO | WO 99/34205 | 7/1999 |

OTHER PUBLICATIONS

Jacobson, S.C. et al., "Fused Quartz Substrates for Microchip Electrophoresis," *Anal. Chem.* (1995) 67:2059-2063.

Manz, A. et al., "Capillary electrohoresis integrated onto a planar microstructure," *Analysis Mag.* (1994) 22(9):25-28.

Manz, A. et al., "Electroosmotic pumping and electrophoretic separations for miniaturized chemical analysis systems," *J. Micromech. Microeng.* (1994) 4:257-265.

Ramsey, J.M. et al., "Microfabricated chemical measurement systems," *Nature Med.* (1995) 1:1093-1096.

Seiler, K. et al., "Planar Glass Chips for Capillary Electrophoresis: Repetitive Sample Injection, Quantitation, and Separation Efficiency," *Anal. Chem.* (1993) 65:1481-1488.

Seiler, K. et al., "Electroosmotic Pumping and Valveless Control of Fluid Flow Within a Manifold of Capillaries on a Glass Chip," *Anal. Chem.* (1994) 66:3485-3491.

Young, J. "Lab on a chip" *Forbes* (Sep. 23, 1996).

* cited by examiner

MICROFLUIDIC DEVICES AND SYSTEMS INCORPORATING COVER LAYERS

CROSS-REFERENCES TO RELATED APPLICATIONS

This application is a continuation-in-part of U.S. Ser. No. 09/544,711, filed on Apr. 6, 2000, now U.S. Pat. No. 6,756,019, which is a continuation-in-part application of U.S. Ser. No. 09/028,965, filed on Feb. 24, 1998, now U.S. Patent No. 6,251,343, the entire contents of which are incorporated by reference herein.

BACKGROUND OF THE INVENTION

As has been the case in the electronics and computer industries, trends in analytical chemical and biochemical instrumentation have been toward miniaturization. In chemical and biochemical analyses, such miniaturization as achieved in e.g., microfluidic systems, provides numerous advantages, including significantly smaller reagent requirements, faster throughput, ready automatability, and in many cases, improved data.

By way of example, U.S. Pat. Nos. 5,498,392 and 5,587,128 describe the performance of amplification reactions in microfabricated devices including microscale flow systems and/or reaction chambers. Such systems substantially reduce the requirements for expensive reagents utilized in amplification reactions. Further, the small scale of these devices also provides for enhanced thermal transfer between heating sources and the reagents in the device.

Similarly, U.S. Pat. No. 5,637,469 describes the use of devices having extremely small internal dimensions for detecting an analyte in a sample via a binding assay. Again, the small scale of such devices provides advantages in terms of small reagent volumes.

Commonly owned Published International Application No. WO 98/00231 describes the use of microfluidic devices and systems in the performance of high-throughput screening assays. Again, these systems reduce the required volumes of potentially very expensive test compounds, e.g., drug candidates, library compounds, etc.

Despite the numerous advantages realized by the miniaturization of analytical systems, such miniaturization can provide difficulties in the use of such systems, including user handling, reagent delivery or filtration, and system interfacing of such devices.

It would therefore be desirable to provide microfluidic devices that capture the advantages associated with extremely small volumes and dimensions, without the problems associated with such small-scale devices. The present invention meets these and a variety of other needs.

SUMMARY OF THE INVENTION

It is a general object of the present invention to provide microfluidic devices and methods that combine the advantages of microfluidics with improved material handling characteristics and reduced costs for manufacturing. The present invention accomplishes this in a first aspect, by providing microfluidic devices that incorporate a body structure comprising at least a first microscale channel network disposed therein. The body structure has a plurality of ports disposed in it, where each port is in fluid communication with one or more channels in the first channel network. The devices also include a cover layer comprising a plurality of apertures disposed therethrough. The cover layer is mated with the body structure whereby each of the apertures is aligned with a separate one of the plurality of ports.

In preferred aspects, each of the body structure and the cover layer separately comprises at least a first surface. The plurality of ports in the body structure are disposed in the first surface of the body structure, and the plurality of apertures in the cover layer are disposed in the first surface of the cover layer. The first surface of the cover layer is mated to the first surface of the body structure such that the apertures align with and are in fluid communication with the ports. In further preferred aspects, the cover layer is fabricated from a polymeric material, and is preferably an injection molded polymeric part.

In one embodiment, the microfluidic devices include a plurality of rings disposed between the cover layer and the body structure with each such ring surrounding one pair of aligned ports and apertures. Each of the rings is optionally molded, e.g., around one or more of the plurality of apertures disposed in the surface of the cover layer and circumferentially around at least one of the plurality of ports aligned with the one or more apertures. Alternatively, the rings are molded around one or more of the plurality of ports disposed in the first surface of the body structure and circumferentially around at least one of the plurality of apertures aligned with the one or more ports. As a further alternative, each of the rings is a separate component from either the cover layer or the body structure; e.g., the rings optionally include a gasket that is placed around one or more port and/or aperture. As separate components, each of the rings is typically placed circumferentially around at least one of the plurality of apertures and circumferentially around at least one of the plurality of ports aligned with one or more of the plurality of apertures.

In another embodiment, the microfluidic devices of the present invention also optionally include a membrane (e.g., a semi-permeable membrane or the like) disposed between at least one pair of aligned apertures and ports, which together form wells, for sieving aggregations of material (e.g., aggregations of cells, molecules, etc.) and/or delivering various reagents to the devices. The membrane is also optionally disposed on or over the wells. The invention additionally includes embodiments in which at least a portion of the wells of the devices include a conductive coating. The use of conductive coatings, inter alia, minimizes cross-contamination between microfluidic devices. Furthermore, the invention also includes other embodiments in which rings, membranes, and/or conductive coatings are used in various combinations in the devices.

The present invention also includes methods of controlling a material composition delivered into a microfluidic device which include flowing a solution that includes the material (e.g., particles, reagents, or the like) through a semi-permeable membrane portion disposed in one or more wells of the devices. Additionally, the methods optionally include immobilizing the material on the semi-permeable membrane prior to delivering the material into the device.

In a related aspect, the present invention provides a microfluidic system that includes a microfluidic device in accordance with the present invention, where the device is further mounted on a controller/detector apparatus that is configured to receive the microfluidic device. The controller/detector apparatus comprises an optical detection system and a material transport system, where the detection system and transport system are operably interfaced with the microfluidic device when the device is mounted on the controller/detector.

DETAILED DESCRIPTION OF THE INVENTION

I. General

Figure 1:
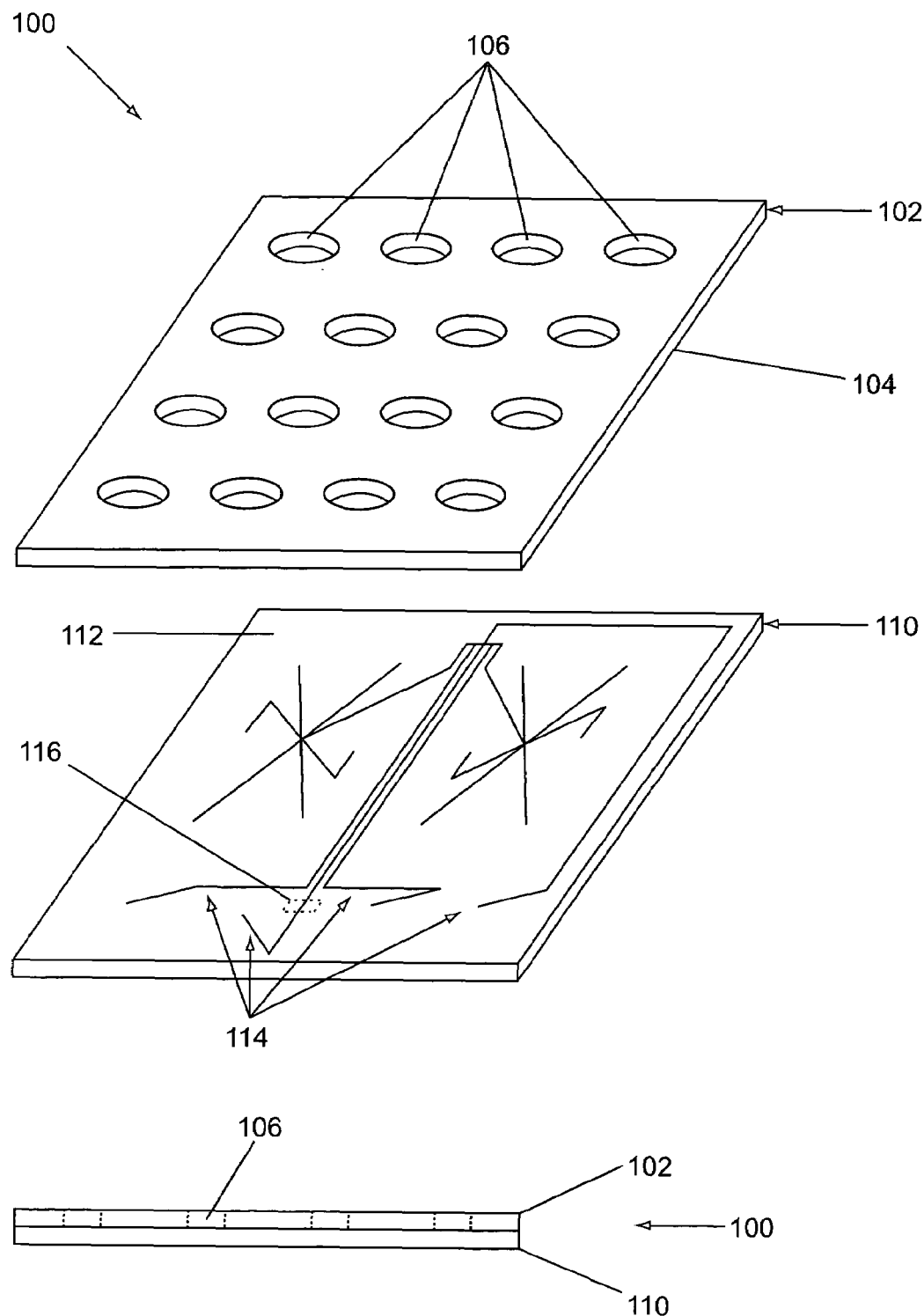
FIG. 1 schematically illustrates a microfluidic device body structure that incorporates a planar layered structure.

The present invention generally provides microfluidic devices and methods that take advantage of the extremely small-scale nature of microfluidic devices and systems, while at the same time, not suffering from some of the potential problems associated with such systems. In particular, the microfluidic devices and systems of the invention include an additional cover layer as a portion of the microfluidic device, e.g., overlaying and attached to the basic body structure of the device. The cover layer employed in the devices of the invention typically comprises a number of apertures disposed through it, which apertures mate with and/or form part of the reservoirs and/or access ports of the microfluidic device. These cover layers provide a number of advantages in the operation and fabrication of microfluidic devices.

As used herein, the terms "microscale," "microfabricated" or "microfluidic" generally refer to one or more fluid passages, chambers or conduits which have at least one internal cross-sectional dimension, e.g., depth, width, length, diameter, etc., that is less than 500 μm, and typically between about 0.1 μm and about 500 μm. In the devices of the present invention, the microscale channels or chambers preferably have at least one cross-sectional dimension between about 0.1 μm and 200 μm, more preferably between about 0.1 μm and 100 μm, and often between about 0.1 μm and 20 μm. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby at least two channels are in fluid communication.

The body structure of the microfluidic devices described herein can take a variety of shapes and/or conformations, provided the body structure includes at least one microfluidic channel element disposed within it. For example, in some cases the body structure has a tubular conformation, e.g., as in capillary structures, such as fused silica or polymeric capillaries that include internal diameters in the microscale range, set forth above. Alternatively, body structures may incorporate non-uniform shapes and/or conformations, depending upon the application for which the device is to be used. In preferred aspects, the body structure of the microfluidic devices incorporates a planar or "chip" structure.

Although in some cases, a single piece body structure, e.g., a capillary, may be used, the devices described herein typically comprise an aggregation of two or more separate layers which when appropriately mated or joined together, form the body structure of the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

FIG. 1 illustrates one example of the body structure of a microfluidic device that incorporates a planar, layered structure. As shown, the body structure 100 includes at least two layers, an upper layer 102 and a lower layer 110. The upper surface 112 of the lower layer 110 is fabricated to include grooves and/or wells 114. The lower surface 104 of the upper layer 102 is then mated to the upper surface 112 of the lower layer 110 such that the grooves and/or channels define channels or conduits, and chambers within the interior of the aggregate body structure.

A variety of substrate materials may be employed as the bottom portion. Typically, because the devices are microfabricated, substrate materials will be selected based upon their compatibility with known microfabrication techniques, e.g., photolithography, wet chemical etching, laser ablation, reactive ion etching (RIE), air abrasion techniques, injection molding, LIGA methods, metal electroforming, embossing, and other techniques. Suitable substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents. In preferred aspects, the substrates used to fabricate the body structure are silica-based, and more preferably glass or quartz, due to their inertness to the conditions described above, as well as the ease with which they are microfabricated.

In alternate preferred aspects, the substrate materials comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Again, such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. Pat. No. 5,885,470, and which is incorporated herein by reference in its entirety for all purposes.

In the embodiment shown, the upper layer 102 of the body structure 100, includes a plurality of ports 106 disposed through it. These ports are positioned to communicate with specific points of the channels or grooves 114, e.g., the termini, in the aggregate body structure when the upper and lower layers are mated. The ports 106 function to provide fluid access to the channels of the device, and in certain aspects, electrical access to the channels within the body structure. As discussed further below, rings are optionally molded around (i.e., surround) one or more of the plurality of ports on the upper surface of the upper layer of the body structure. Additionally, at least a portion of the ports also optionally includes a conductive coating so that electrical communication is optionally achieved in the device without placing electrodes directly into, e.g., the ports. The use of conductive coatings is also described further below.

In many embodiments, the microfluidic devices include an optical detection window 116 disposed across one or more channels and/or chambers of the device. Optical detection windows are typically transparent such that they are capable of transmitting an optical signal from the channel/chamber over which they are disposed. Optical detection windows may merely be a region of a transparent layer of the body structure, e.g., where the layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

Microfluidic devices may be used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. Alternatively, these devices may be coupled to a sample introduction port, e.g., a pipettor, which serially introduces multiple samples into the device for analysis. Examples of such sample introduction systems are described in e.g., U.S. patent application Ser. No. 08/761,575 which was filed on Dec. 6, 1996 and U.S. Pat. No. 5,880,071, each of which is hereby incorporated by reference in its entirety for all purposes. As discussed below, the invention also includes methods and devices that utilize membranes for sieving aggregations of material (e.g., clumps of cells, reagents, or other particles) and otherwise delivering reagents or other materials into the ports of the devices.

In preferred aspects, the microfluidic devices of the present invention utilize electrokinetic material transport systems to direct and transport materials through the channels of the device. As used herein, "electrokinetic material transport" generally refers to systems and methods for transporting and directing materials within an interconnected channel and/or chamber containing structure, through the application of electrical fields to the materials, thereby causing material movement through and among the channels and/or chambers, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure, either alone, or in conjunction with the electrophoretic forces previously described, which electroosmotic flow results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, producing a concentration of protons near the fluid/surface interface, and creating a positively charged sheath surrounding the bulk fluid in the channel. Application of a voltage gradient across the length of the channel, causes the proton sheath to move in the direction of the voltage drop, i.e., toward the negative electrode. Flow in the opposite direction is achieved by either reversing the voltage gradient, or by providing a channel bearing positively charged ionizable groups, e.g., amino groups, etc.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves that include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left:top, to left:right. The amount of time and the voltage gradient applied dictates the amount of material that will be dispensed in this manner.

In particularly preferred aspects, electrokinetic material transport is controlled through the application of appropriate currents through the channels of the system, in order to propagate material movement therethrough. The use of current control in electrokinetic material transport systems is described in detail in commonly owned U.S. Pat. No. 5,800,690 and Published PCT Application No. 98/00707, both of which are incorporated herein by reference. In brief, in electrokinetic material transport systems, the relative potentials at the intersections of the channels dictates the direction and velocity of material movement at those intersections. Control of these potentials has typically relies upon the calculation of applied voltages based upon the desired potential at the intersections and the resistance of the channel between the intersection and the electrodes at which voltages are applied. By monitoring and controlling the current, the potential at the intersection is maintained at the desired level, and the applied voltages are self-regulating.

Although described for the purposes of illustration with respect to a four way, cross intersections, these controlled electrokinetic material transport systems can be readily adapted for more complex interconnected channel networks, e.g., arrays of interconnected parallel channels. As discussed further below, electrokinetic material transport systems also optionally include the use of conductive coatings to achieve electrical communication.

A. Physical and Electrical Isolation of Reservoirs/Ports

As noted previously, in the design and fabrication of microfluidic systems, and underlying goal is to miniaturize the entire system. This is typically done either to reduce volume, increase the speed of the operation, or multiplex the particular operation, e.g., incorporate multiple operations within the same unit space occupied by the device. In accomplishing these goals, however, the channel networks that effectively define the functional space of a given microfluidic system become much smaller. As a result of smaller channel networks, or more complex networks being incorporated into the same unit space, the access points for these channel networks, e.g., reservoirs, electrical access ports and the like, are drawn closer and closer together.

As these access ports are drawn closer together, it becomes more difficult to practically isolate one port from another. For example, where the access ports are used to introduce fluids into the channel networks of the system, the closer the ports are together or the smaller they become, the more difficult it becomes to introduce fluid volumes separately into different ports. This is true for manual introduction of fluids, e.g., using a pipettor, as well as automatic methods, e.g., using robotic fluid handling systems.

In a similar problem, as access ports are placed closer together, it also becomes more difficult to isolate those ports electrically. This is of particular importance in microfluidic systems that utilize electrical systems operably coupled to the channel networks, such as in electrical sensing systems, e.g., amperometric, potentiometric, etc., and/or electrokinetic material transport that are used for transport of materials through the channel networks, as described above. In particular, where the ports of the system are used for electrical access, the possibility of bridging currents, or "shorts," between two or more adjacent or at least proximal electrodes increases, e.g., across the surface of the device as a result of fluids, dirt or oils deposited on the surface of the device.

The present invention generally addresses these problems by providing microfluidic devices that include a cover layer that provides an effective barrier between neighboring reservoirs, to prevent fluid and/or electrical links from forming between neighboring electrodes. The barrier optionally includes a ridge around each of the reservoirs, e.g., an annular ridge surrounding a circular reservoir. The ridge has the effect of preventing fluid 'spill-over' from one well entering into another adjacent well. Similarly, the ridge effectively creates a longer path length across which any electrical bridging current, e.g., short circuit, must travel. Typically, these ridges extend at least 0.1 mm from the surface of the cover layer, preferably, at least 1 mm and in some cases, at least 2 mm or more, from the upper surface of the cover layer. In many cases, the barrier, e.g., as provided by the ridge structure, will increase the effective path length between neighboring wells by at least 1.5×, preferably at least 2×, and often at least 3-5× over that provided by the reservoirs in the body structure, alone.

The use of separate or integrated holding structures for microfluidic devices is described in commonly owned U.S. Pat. No. 5,876,675 and incorporated herein by reference in its entirety for all purposes.

In addition to providing an effective barrier between neighboring reservoirs, in some cases, the upper surface comprises a hydrophobic material to prevent deposition/aggregation of fluids on that surface which might physically or electrically contaminate neighboring reservoirs. In such cases, a hydrophobic material, e.g., a polymer, is coated on the surface of the cover layer. Preferably, however, and as described in greater detail below, the cover layer itself is fabricated from a hydrophobic polymer material.

B. Increased Volume Capacity of Reservoirs

The cover layer component of the microfluidic devices of the present invention also provides the capability to increase the volume capacity of the reservoirs of those devices. In particular, the apertures disposed in the cover layer can increase the total depth of the fluid reservoirs of the device by extending those reservoirs. While fluid volume is not a critical limitation in many microfluidic applications, there are some instances where substantial variations in fluid volume from, e.g., evaporation, can have an effect on a particular operation. This is typically due to concentration of one or more solutes within the fluids, e.g., salts, enzymes, etc. By increasing the fluid volume capacity of the reservoirs, one can substantially mitigate any effects resulting from a partial evaporation of fluids by reducing the percentage of evaporation.

Typically, the apertures disposed in the cover layer add to the depth of the reservoirs in the body structure. In doing so, the apertures are typically at least 1 mm deep, preferably at least 2 mm deep, and often at least 5 mm deep. This typically results in reservoirs in the overall device, e.g., from the combination of the ports in the body structure and the apertures in the cover layer, having volumes of at least 5 μl, preferably at least 10 μl, more preferably at least 20 μl, often at least 50 μl, and in some cases, at least 100 μl. In any event, the volume of the reservoirs of the overall device will typically fall in the range between about 1 and about 200 μl, preferably between about 2 and 100 μl, more preferably between about 5 and about 100 μl, and still more preferably, between about 5 and 50 μl.

II. Fabrication of Cover Layers

The cover layer aspect of the microfluidic devices described herein may generally be fabricated from any of a number of different materials using a number of different methods. For example, the materials and methods described above in the manufacture of the microfluidic elements of the device may also be employed in the manufacture of the cover layer. While these methods are effective, in preferred aspects, more conventional manufacturing techniques are used to produce the cover layer. In particular, because the cover layer does not need to be manufactured to the tolerances of the microfluidic elements of the devices of the invention, they can generally be manufactured using less precise and less expensive or time consuming methods and from less costly materials.

For example, in a layered microfluidic device fabricated from two glass layers, fabrication of the ports or reservoirs in one layer, e.g., by drilling or air abrasion techniques, can take a substantial amount of time. Further, the amount of time required for such fabrication increases in a non-linear, e.g., exponential, fashion with increasing substrate thickness. Conversely, reduction of substrate thickness reduces the amount of time required to fabricate the reservoirs, in an exponential fashion. Because a portion of the volume of the reservoirs in the final microfluidic device is optionally supplied by the cover layer element, the substrate layers used to fabricate the body structure of the microfluidic device can be substantially thinner. Specifically, less of the total desired volume of the reservoir is a function of substrate thickness. As a result, fabrication time and cost associated with the manufacturing of reservoirs in the body structure are substantially reduced.

Typically, the cover layer comprises an injection molded polymeric or plastic part, fabricated from any of a number of different manufacturable plastics. For example, the cover layer is typically fabricated from any of the polymeric materials described above for fabricating the body structure of the microfluidic device, e.g., polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS, and the like. In alternate aspects, the cover layer is optionally fabricated from non-polymeric materials, e.g., silica-based substrates, such as glass, quartz, silicon, as well as ceramics or metals.

Attachment of the cover layer to the body structure of the device is also typically accomplished by well known methods, including adhesive bonding, ultrasonic welding, solvent welding, thermal bonding, and the like. In preferred aspects, the cover layer is attached to the body structure of the device using an adhesive material, and more preferably, U.V. curable adhesives are used to join the cover layer with the body structure. Such adhesives are generally commercially available, e.g., from 3M Corporation. In particularly preferred aspects, the selected adhesive is electrically insulating, e.g., nonconductive, non-soluble and/or non-leaching in application buffers, low fluorescing, and the like.

In a preferred embodiment of the present invention, the microfluidic device includes a plurality of rings disposed around the reservoirs or ports in the microfluidic device underlying the cover layer. The rings are optionally molded around the apertures on the first surface of the cover layer and integral with the cover layer. Alternatively, the rings are molded around the ports disposed in the first surface of the body structure and integral with the body structure. As an additional alternative, the rings are separate from the cover layer and the body structure. Upon attachment of the cover layer to the body structure, a ring becomes disposed between each aperture aligned with each port. As discussed further below, the rings also optionally include conductive coatings and/or membranes.

Figure 4A:
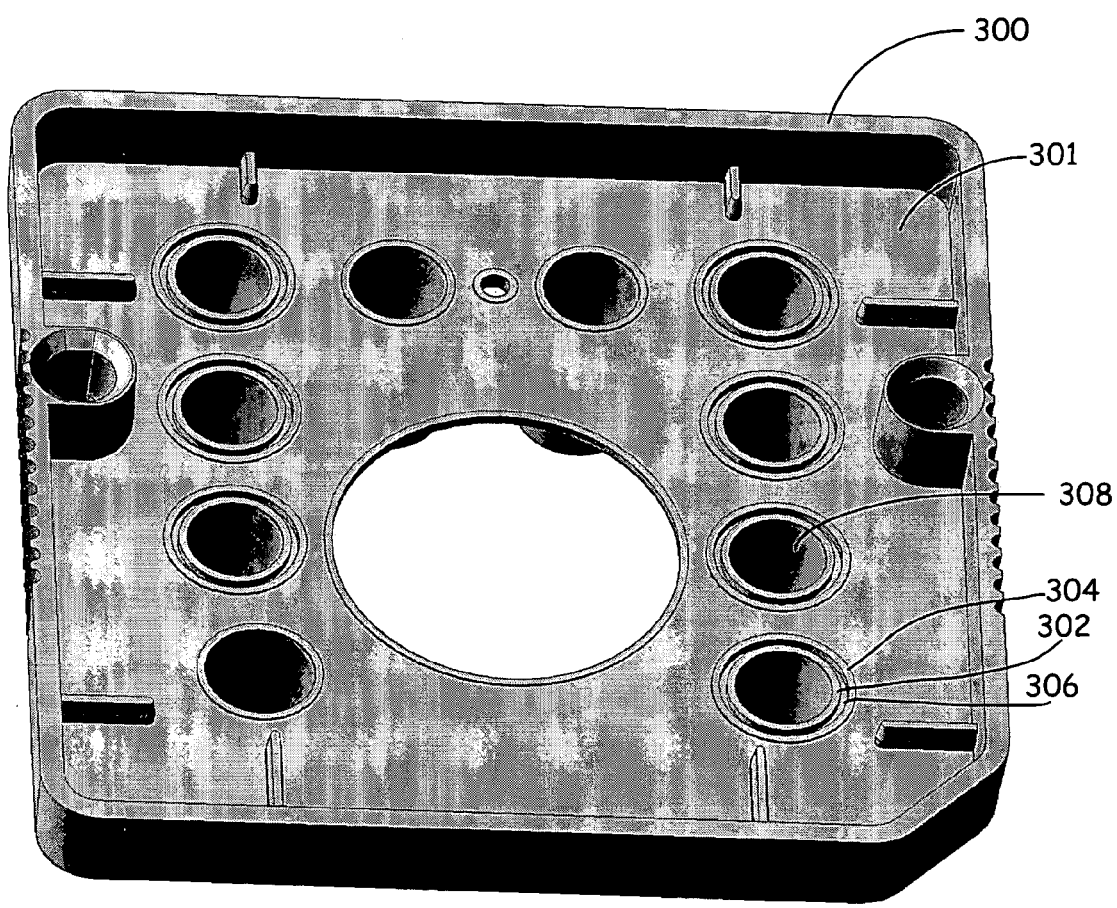
FIG. 4A is a perspective view of an alternative embodiment of a cover layer according to the teachings of the present invention which includes a double ring structure disposed on the underside surface of the cover layer. The rings are separated by an annular groove or moat which helps to minimize adhesive (or other bonding material) leakage into the ports of the microfluidic device when the cover layer is bonded to the body structure of the microfluidic device.
Figure 4B:
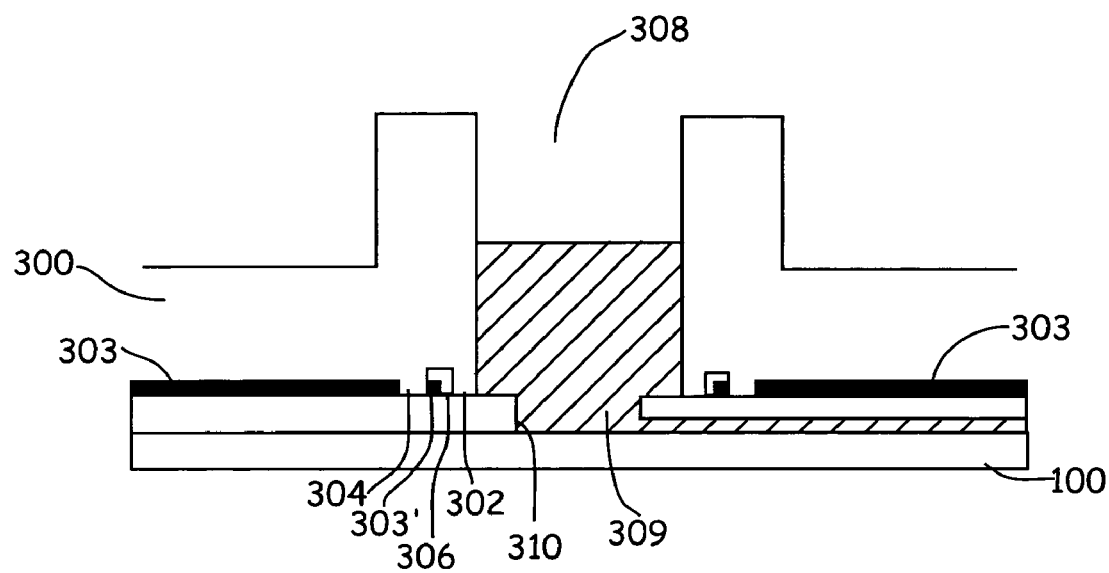
FIG. 4B is a side cross-sectional view of the cover layer embodiment of FIG. 4A.

In a further alternative embodiment as show in FIGS. 4A-B, the cover layer 300 includes at least two annular rings 302, 304 circumferentially disposed around each fluid port or well 308 disposed in the first (underside) surface 301 of the cover layer and integral with and extending downwardly from the first surface of the cover layer. The inner ring 302 and outer ring 304 are preferably separated by an annular groove or moat 306, as best seen in FIG. 4B. The double ring and moat structure of FIGS. 4A-B helps to further minimize the leakage of adhesive 303 (or other bonding material and/or solvent, e.g. in the case of solvent bonding techniques) into the wells of the microfluidic device when the cover layer is bonded to the body structure 100 of the microfluidic device. The annular groove or moat 306 creates an annulus of trapped air between the inner and outer rings 302, 304 which helps to isolate any adhesive (e.g., 303' in FIG. 4B) that may leak past the outer ring 304. Subsequently, when the wells 308, 310 of the cover layer and body structure of the microfluidic device, respectively are filled with a liquid 309, the liquid in the well and the adhesive are kept separated by the annulus.

The cross-sectional dimensions of the annular rings 302, 304 and the annular groove or moat 306 may vary depending on a number of factors, such as the viscosity of the bonding material (e.g., adhesive and/or solvent) used, the capillarity of the bonding material, the level of force which is applied to the cover layer 300 and body structure 100 to cause the formation of the bond between them, etc. At a minimum, the dimensions of the annular groove 306 should be designed to be of sufficient depth (and width) such that when the cover layer 300 is bonded to the body structure 100 of the microfluidic device, the adhesive only wicks up to the outer edge of the annulus where it forms a dam at that interface, and therefore does not propagate all the way to the edge of the well 308. For example, empirically, it has been determined that in connection with the use of an epoxy adhesive bonding material such as EM Cast 1822 available commercially from Electronic Materials, Inc. (Breckenridge, Colo.), that the width of annular rings 302, 304 should be between about 0.001 and 1.0 mm, preferably between about 0.2 and 0.7 mm, for example between about 0.4 and 0.5 mm wide. The depth of the annular rings 302, 304 (e.g., the distance at which the rings extend below the lower surface 301 of the cover layer 300) should be sufficient such that a liquid bonding material (e.g., adhesive) can wick between the lower surface of the cover layer and the top of the body structure 100 when the cover layer is mated to the body structure. Generally, it has been found that the depth of the annular rings 302, 304 should be at least about 0.1 mm, for example between about 0.1 and 0.6 mm, for example between about 0.3 and 0.5 mm. The annular groove or moat 306 should have a width of between about 0.001 and 1.0 mm, preferably between about 0.2 and 0.8 mm, for example between about 0.4 and 0.5 mm wide, and have a depth dimension of between about 0.001 and 1.0 mm, preferably between about 0.25 to 0.5 mm, e.g., about 0.3 mm deep.

The rings act to prevent adhesive, e.g., U.V. curable adhesive (mentioned above), from getting into the ports and in turn from contacting any assay components that are in the ports. As such, rings are optionally shaped as circular rings or as any other functionally equivalent forms, e.g., rectangular or polygonal rings. In the context of rings, the terms "thick" and/or "thickness" refer to the distance from an inner edge to an outer edge of a ring. A ring has a single thickness, as in the case of circular rings, or multiple thicknesses when other ring shapes are selected. However, each ring typically has a thickness in the range of from about 1 µM to about 1,000 µM. For example, the rings are optionally in the range of from about 50 µM to about 750 µM thick, e.g., about 500 µM thick. Larger rings typically result in the creation of voids around the ports/apertures. Narrower rings, e.g., in the range of from about 100 µM to about 500 µM are generally preferred.

The rings are optionally fabricated from many different materials. For example, if they are integral with the cover layer or the body structure, they are made from the same material, and in the same step, as either of those two respective components. As discussed above, these optionally include a wide variety of polymeric and non-polymeric materials. If the rings are separate from the cover layer and the body structure, they are also optionally fabricated from any of the polymeric or non-polymeric materials discussed above as well as others, including polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), glass, quartz, silicon, gallium arsenide, silicon oxide, ceramics, metals, latex, silicone, or the like.

In alternate aspects, the body structure is attached to the cover layer via a clamping mechanism. In such aspects, an optional flexible gasket, e.g., latex, silicone, etc., is placed between the upper surface of the body structure and the lower surface of the cover layer. The flexible gaskets also optionally include the rings, discussed above, as integral components therein. The body structure is then compressively clamped against the cover layer forming a sealed, joined structure. Suitable clamping mechanisms may be separate from the body structure/cover layer assembly, i.e., screw clamps, clip-style clamps, e.g., that clamp the edges of the body structure and cover layer, and the like. Alternatively, integrated clamping mechanisms are provided as a portion of the cover layer, into which the body structure is snapped. Such clamping systems are described in greater detail below, with reference to FIG. 3B.

III. Microfluidic Devices and Methods Incorporating Membranes and/or Conductive Coatings In general, the process of developing operable and commercially valuable microfluidic devices typically includes overcoming various technical hurdles. For example, one technical problem in the development of practical cell-based microfluidic assays has been eliminating cell clumps or aggregations that clog microscale channels, rendering the devices inoperable. Another challenge has been to create functional reagent delivery systems for integrating reagents into microfluidic devices such that they will dissolve, e.g., in a sample. An additional problem has been cross-contamination among microfluidic devices when, e.g., electrodes are used in multiple devices. The present invention provides various solutions to all of these technical problems; solutions which are optionally used alone or in combination in the same device.

For example, the present invention provides methods of controlling a material composition delivered into a microfluidic device. The methods include providing a channel network disposed in the microfluidic device and at least one well in fluid communication with the channel network. The well includes a semi-permeable membrane portion disposed therein or thereon. As a first option, the methods also include flowing a first solution that includes a material (e.g., particles, reagents, or the like) into the well through the semi-permeable membrane portion. A second option includes immobilizing the material on the semi-permeable membrane portion and flowing a second solution into the well of the microfluidic device. Thereafter, the second option includes mixing the second solution and the material immobilized on the semi-permeable membrane portion such that at least some of the material dissolves in the second solution and enters the microfluidic device through the semi-permeable membrane portion. The mixing step optionally includes a physical technique, such as shaking, vortexing, centrifuging, etc. the microfluidic device to dissolve at least some of the material adhered to the semi-permeable membrane portion in the second solution. In either case, the channel network is at least partially filled with a fluid prior to flowing the first or second solutions into the well, or the channel network is void of fluid prior to flowing the first or second solutions into the well.

Irrespective of the option selected, aggregations of the material are sieved and prevented from entering the channel network of the microfluidic device. As used herein, the phrase "aggregations of material" refers to clumps or clusters of the material, such as a clump of cells, reagent molecules, or the like, which, if permitted to enter the device, would likely obstruct the channel network. The semi-permeable membranes utilized selectively exclude aggregations of material based upon size. Typically, the semi-permeable membrane portion includes a pore size of at least about 0.1 nm. In preferred embodiments, the semi-permeable membrane portion includes a pore size of between about 10 µm and about 100 µm, which will exclude clumps of cells. The membranes optionally cover at least a portion of a well and are disposed between the body structure and the cover layer so as to keep each well sealed from other wells. Alternatively, membranes are placed on or over wells.

Suitable semi-permeable membrane portions optionally include, e.g. a woven mesh membrane, a microfiltration membrane, a nanofiltration membrane, a dialysis membrane, an electrodialysis membrane, a prevaporation membrane, a reverse osmosis membrane, an ultrafiltration membrane, a composite membrane, a charged membrane, a conductively-coated membrane, a hydrophilic membrane, a hydrophobic membrane, a polymer-based membrane, a non-polymer-based membrane, a porous plastic matrix membrane (e.g., POREX® Porous Plastic, etc.), a porous metal matrix membrane, a polyethylene membrane, a poly(vinylidene difluoride) membrane, a polyamide membrane, a nylon membrane, a ceramic membrane, a polyester membrane, a metal membrane, a polytetrafluoroethylene (TEFLON™) membrane, a polyaramide membrane, a polycarbonate membrane, a powdered activated carbon membrane, a polypropylene membrane, a glass fiber membrane, a glass membrane, a nitrocellulose membrane, a cellulose membrane, a cellulose nitrate membrane, a cellulose acetate membrane, a polysulfone membrane, a polyethersulfone membrane, a polyolefin membrane, or the like. A number of publications relating to membranes are also available, including Cheryan, *Ultrafiltration and Microfiltration Handbook* ($2^{nd}$ Ed.) Technomic Publishing Company, Lancaster, Pa. (1998), Mulder, *Basic Principles of Membrane Technology* ($2^{nd}$ Ed.) Dordrecht: Kluwer (1996), and Ho and Sirkar (Eds.), *Membrane Handbook* Van Nostrand Reinhold, N.Y. (1992).

The methods of the present invention include various materials. In preferred embodiments, the material includes a particle, such as a cell or a set of cells. For example, the material flowed into the well typically includes a plurality of cells or sets of cells and the volume of the first solution flowed into the well is optionally between about 0.5 and about 20 µl, optionally in the range of from about 5 to about 15 µl, or, e.g., about 10 µl. Cell sample volumes loaded into wells in this range are vast improvements over the several hundreds of microliters typically used, e.g., in conventional cell filtration techniques. The material also optionally includes a reagent, such as an atom, a set of atoms, a molecule, a set of molecules, a bead, a set of beads, a functionalized bead, a set of functionalized beads, an antigen, a set of antigens, a protein, a set of proteins, a peptide, a set of peptides, an enzyme, a set of enzymes, a nucleic acid, a set of nucleic acids, a lipid, a set of lipids, a carbohydrate, a set of carbohydrates, an inorganic molecule, a set of inorganic molecules, an organic molecule, a set of organic molecules, a drug, a set of drugs, a receptor, a set of receptors, a ligand, a set of ligands, an antibody, a set of antibodies, a neurotransmitter, a set of neurotransmitters, a cytokine, a set of cytokines, a chemokine, a set of chemokines, a hormone, a set of hormones, or the like.

As mentioned, the methods of controlling material compositions optionally include immobilizing the material (e.g., a labeled antibody, a reagent, or other particle) on the semi-permeable membrane portion before delivering the material into the microfluidic device. Materials are alternately immobilized using various techniques or combinations of techniques. Additionally, the immobilizing step is optionally performed prior to placing the semi-permeable membrane portion on the at least one well. In a preferred embodiment, the immobilizing step includes dehydrating the first solution that includes the material on the semi-permeable membrane portion such that at least some of the material adheres to the semi-permeable membrane portion. This immobilization approach optionally includes, e.g., air drying, heat drying, lyophilizing, using a drying reagent, or the like to dehydrate the first solution. As mentioned, this technique optionally includes, e.g., spotting and dehydrating the first solution containing the material on the semi-permeable membrane before placing the membrane over the well(s).

In another embodiment, the semi-permeable membrane portion includes a hydrophobic coating, or is composed of a hydrophobic substance, and the material is a hydrophobic material so that the material immobilizes on the semi-permeable membrane portion by hydrophobic attraction. Similarly, the semi-permeable membrane portion optionally includes a hydrophilic coating, or is composed of a hydrophilic substance, and the material is a hydrophilic material so that the material immobilizes on the semi-permeable membrane portion by hydrophilic attraction. Many hydrophobic and hydrophilic coatings or substances are known and are optionally used in the methods and devices of the present invention. For example, suitable hydrophobic coatings or substances optionally include, e.g., hydrophobic polymers, fluorocarbon polymers, chlorinated polysiloxanes, polytetrafluoroethylenes (TEFLON™), polyglycines, polyalanines, polyvalines, polyleucines, polyisoleucines, chlorine terminated polydimethylsiloxane telomers, bis(perfluorododecyl) terminated poly(dimethylsiloxane-co-dimer acids), derivatives thereof, or the like. TEFLON™ is generally preferred and is readily available from various commercial sources. Appropriate hydrophilic coatings and substances optionally include, e.g., hydrophilic polymers, polyimides, polyethylene oxides, polyvinylpyrrolidone, polyacrylates, hydrophilic polysaccharides, hyaluronic acids, chondroitin sulfates, derivatives thereof, or the like.

Other immobilization techniques include, e.g., providing the semi-permeable membrane portion to include a net charge. In turn, the material includes a net charge opposite from the semi-permeable membrane portion so that the material immobilizes on the semi-permeable membrane portion by electrostatic attraction.

The present invention also relates to a microfluidic device that includes a membrane (e.g., a semi-permeable membrane portion) disposed between at least a portion of the first surface of the cover layer and the first surface of the body structure such that the membrane is disposed between at least one pair of aligned apertures and ports. Aspects of this device are optionally utilized, inter alia, for controlling material (e.g., reagents, cells, or other particles) compositions delivered into the device. The type of semi-permeable membrane portion used, including the pore size, optionally include any of those described above.

As mentioned, in certain cases cross-contamination among microfluidic devices results, e.g., when electrodes are used in multiple microfluidic devices. This form of contamination typically occurs when electrodes are placed directly into liquids situated in the wells of the devices. To address this problem, the present invention optionally includes the use of conductive coatings that permit the use of dry contact electrodes to minimize this type of contamination. Conductive coatings are optionally deposited by, e.g., plating, electroforming, vapor deposition, or the like. A conductive coating also optionally includes, e.g., a pre-formed piece of metal or other conductive material pressed into one or more wells of a device such that the coating covers at least a portion of the internal surface of, and extends over the top rim of, one or more wells. The conductive coating optionally includes, e.g., a thin ring (or other functionally equivalent form) of conductive material pressed into one or more wells of a device so that conductive communication is optionally established between the microchannels of the device and a conductive source. Suitable conductive coatings are discussed further below.

In one embodiment, each of the plurality of ports includes a rim disposed circumferentially around each port in the first surface of the body structure and an internal surface in which at least a portion of the rim and the internal surface of at least one of the plurality of ports includes a conductive coating. In this embodiment, conductive contact between the conductive coating and an electrode is optionally established, e.g., by modifying the cover layer to include a conductive inlet that is not in fluid communication with the well, yet which is in conductive communication with the conductive coating disposed on the rim and/or internal surface of a port. The rim typically includes at least one width that extends from an edge of each of the plurality of ports of, e.g., at least about 1 μm.

In another embodiment, a membrane (e.g., a semi-permeable membrane portion) is also optionally disposed between at least a portion of the first surface of the cover layer and the first surface of the body structure such that the membrane is disposed between a pair of aligned apertures and ports. A portion of the membrane disposed between the pair of aligned apertures and ports is optionally conductively connected to the conductive coating. The type of semi-permeable membrane portion used, including the pore size, optionally includes any of those described above. In this embodiment, the cover layer also optionally includes an inlet to permit a conductive source (e.g., an electrode) to conductively communicate with the conductive coating.

The microfluidic device of the present invention also typically include a cover layer that includes a second surface opposite the first surface in which each of the plurality of apertures extends from the first surface to the second surface. The plurality of apertures include a rim disposed circumferentially around each aperture in the second surface of the cover layer and an internal surface in which at least a portion of the rim and the internal surface of at least one of the apertures optionally include a conductive coating. The rim generally includes at least one width that extends from an edge of each of the plurality of apertures of, e.g., at least 1 μm. In this embodiment, a membrane is optionally disposed between at least a portion of the first surface of the cover layer and the first surface of the body structure such that the membrane is disposed between at least one pair of aligned apertures and ports. Furthermore, at least a portion of the membrane is also optionally conductively connected to the conductive coating.

As discussed above, the microfluidic devices of the present invention optionally include a plurality of rings that act to prevent adhesive (e.g., U.V. curable adhesive) from getting into the ports and, in turn, from contacting assay components in the ports. The rings are optionally molded around the apertures on the first surface of the cover layer and are integral with the cover layer. Alternatively, the rings are molded around the ports disposed in the first surface of the body structure and are integral with the body structure. As an additional alternative, the rings are separate from the cover layer and the body structure. In any case, the device optionally includes a membrane (e.g., a semi-permeable membrane portion) disposed between at least a portion of the first surface of the cover layer and the first surface of the body structure. The membrane is typically disposed between at least one pair of aligned apertures and ports such that at least a portion of at least one surface of the plurality of rings includes the membrane. Furthermore, the type of semi-permeable membrane portion used, including the pore size, optionally includes any of those described above.

In another embodiment involving conductive coatings, an aligned port, ring, and aperture define a well which includes a rim disposed circumferentially around the well in the annular ridge on a second surface of a cover layer and an internal surface. The rim and the internal surface of at least one well optionally include a conductive coating. To minimize cross-contamination conductive communication is optionally established simply by, e.g., contacting an electrode to the conductively coated rim of the well instead of inserting the electrode into the liquid in the well. The rim typically includes at least one width that extends from an edge of each well of, e.g., at least 1 μm.

In this embodiment, the cover layer optionally includes an inlet such that a conductive source (e.g., an electrode) is capable of conductively communicating with the conductive coating. This device also optionally includes a membrane (e.g., semi-permeable membrane portion) disposed between at least a portion of the first surface of the cover layer and the first surface of the body structure. The membrane is optionally disposed, e.g., between a pair of aligned apertures and ports such that at least a portion of at least one surface of a ring includes the membrane. An additional option includes disposing the membrane over at least one annular ridge surrounding at least one aperture on the second surface. The type of semi-permeable membrane portion used, including the pore size, optionally includes any of those described above. Additionally, at least a portion of the membrane disposed between the pair of aligned apertures and ports is optionally conductively connected to the conductive coating.

In any embodiment of the present invention that includes a conductive coating (e.g., single or multilayered coatings), that coating optionally includes, e.g., a thermally conductive coating and/or an electrically conductive coating (including, e.g., semiconductive and/or superconductive coatings). Essentially any conductive coating is optionally used including, e.g., a metal-containing conductive coating, a metalloid-containing conductive coating, and/or a metal-metalloid-containing conductive coating. As mentioned above, conductive coatings are optionally deposited by, e.g., plating, electroforming, vapor deposition, conductive particle dispersion, or the like. These and other techniques are generally known in the art.

Suitable metals for use in conductive coatings include, e.g., Li, Be, Na, Mg, K, Ca, Sc, Ti, V, Cr, Mn, Fe, Co, Ni, Cu, Zn, Ga, Rb, Sr, Y, Zr, Nb, Mo, Tc, Ru, Rh, Pd, Ag, Cd, In, Sn, Cs, Ba, La, Hf, Ta, W, Re, Os, Ir, Pt, Au, Hg, Tl, Pb, Bi, Fr, Ra, Ac, the lanthanides, the actinides, and compounds and/or combinations thereof. Metalloids (or semi-metals) for use in, e.g., metalloid-containing conductive coatings optionally include, e.g., Al, Ge, As, Po, B, Si, Te, At, and compounds and/or combinations thereof. The coatings alternatively include alloys including both metals and metalloids (i.e., metal-metalloid-containing conductive coatings). Conductive coatings also optionally include, e.g., carbon and graphite, metal salts such as metal oxides and sulfides, metal hydrides, conductive organic polymers (e.g., polyacetylenes, polypyrroles, polyanilines, polythiophenes, derivatives thereof, etc.), or the like. Many such coatings are known in the art and are readily available from commercial sources.

IV. Illustrated Embodiment

Figures 2A, 2B, 2C:
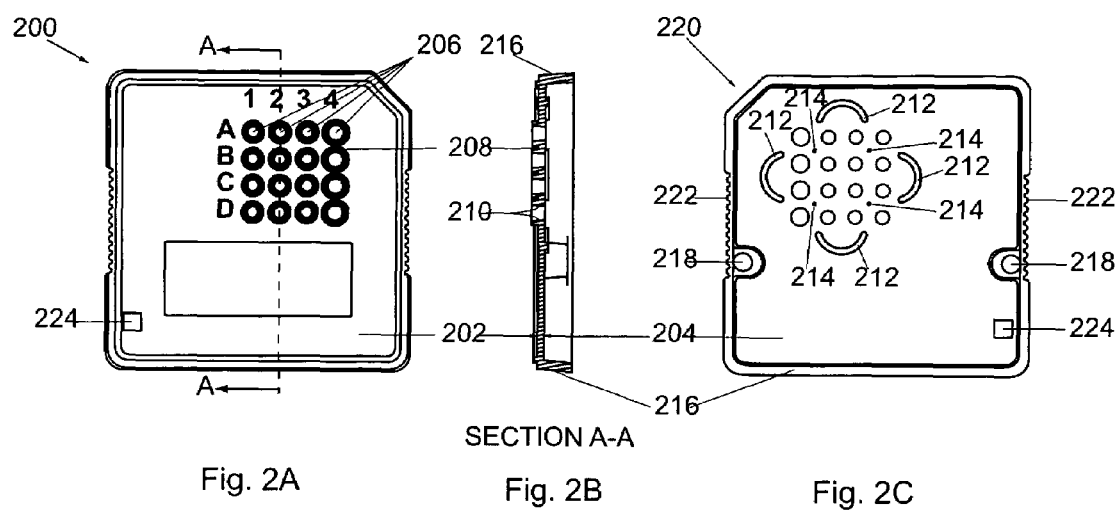
FIGS. 2A-E illustrate from a number of perspectives an embodiment of a cover layer for incorporation in a microfluidic device in accordance with the present invention.
Figure 2D:
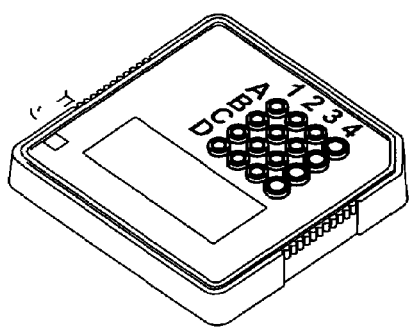
Figure 2E:
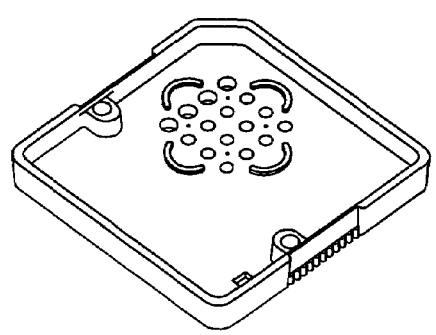

One aspect of the cover layer used in conjunction with the microfluidic devices of the present invention is shown in FIG. 2, from the top (FIG. 2A), side (FIG. 2B), bottom (FIG. 2C), top perspective (FIG. 2D) and bottom perspective views (FIG. 2E). As shown, the cover layer 200 is planar in shape having an upper planar surface 202 and a lower planar surface 204. Also included are a plurality of apertures 206 disposed through the cover layer, e.g., from the upper to lower planar surfaces. Apertures 206 are positioned within the cover so as to align with ports/reservoirs in the body structure of a microfluidic device (e.g., as shown in FIG. 1) when that body structure is mated to the lower planar surface 204 of cover layer 200. Although not shown, rings are also optionally disposed between and surrounding the aligned apertures and ports, to prevent adhesive, e.g., U.V. curable adhesive, from getting into the ports and in turn from contacting assay components that are in the ports, as described herein. As additionally discussed herein, but not shown, membranes (e.g., semipermeable membranes) are optionally disposed between aligned apertures and ports for use in controlling material compositions within the devices, such as by sieving aggregations of materials (e.g., clumps of cells, particles, reagents, etc.) and delivering material into the devices. Conductive coatings are also optionally used, e.g., to minimize cross-contamination among devices.

As shown, the apertures 206 in cover layer 200 are provided in a gridded pattern to match a similar gridded pattern of ports on the body structure of the device. Typically, the gridded arrangement of apertures and ports (collectively, reservoirs) are positioned on regular centers, e.g., 9 mm, 4.5 mm etc., to match the spacing of typical multi-well plates, e.g., 96-well, 384-well, 1536-well, etc.

As shown, an annular ridge 208 is provided on the upper surface 202 of the cover layer 200, surrounding each separate aperture 206. This ridge provides a barrier between neighboring reservoirs in the overall device and also functions to increase the effective volume of each reservoir in the resulting device. In addition, the apertures 206 in the cover layer are optionally provided with tapered walls 210, which are wider at the upper surface and narrower at the lower surface. The tapered walls allow the apertures to perform a funnel-like function, in the introduction of fluids into the ports of the microfluidic devices. Specifically, wider openings facilitate introduction of fluids into the reservoir. The walls of an aperture and a rim disposed in an annular ridge also optionally include a conductive coating.

Also as shown, the lower planar surface 204 of the cover layer 200, has fabricated thereon, a series of raised ridges 212, which function as alignment structures to ensure the body structure of the microfluidic device 100 (from FIG. 1), is properly aligned with the cover layer during the bonding or mating process. Although illustrated as ridges, it will be understood that a number of different alignment structures may be provided upon the lower planar surface for aligning the body structure of the device with the cover layer. For example, a recessed region, which is configured to fit the body structure may be used, whereby placement of the body structure into the recessed region positions the body structure to be appropriately aligned with the apertures in the cover layer. Alternatively, alignment pins may be provided extending from the lower surface, against which the body structure may rest, when appropriately aligned with the cover layer.

Also included on the lower surface 204 of the cover layer 200 are small high spots 214. These high spots, or bumps, maintain the body structure in a position slightly set off of the lower surface 204 when the body structure is mated with the cover layer. The small set off resulting from high spots 214 allows a bonding adhesive material to wick into the space between the body structure and the cover layer for attaching the body structure to the cover layer.

As shown, the cover layer 200 includes side-walls 216, which extend from the lower planar surface 204, effectively creating a hollow-backed structure. This hollow-backed structure permits the mounting of a body structure of a microfluidic device to the lower surface of the cover layer without altering the overall profile of the cover layer, e.g., permitting the combined device-cover layer to be laid flat upon a surface or stacked with other like devices, as well as providing benefits in manufacturing, e.g., curing/hardening of molded parts, etc.

In addition to providing alignment structures for mounting a body structure to the cover layer, as shown, the cover layer also includes additional alignment structures 218 and 220. These alignment structures permit the appropriate alignment of the overall device into an appropriate base unit, such as a controller/detector instrument (not shown). In particular, alignment holes 218 provided disposed through the cover layer are complementary to alignment pins that are provided on a controller/detector instrument (not shown). By matching the pins of the controller/detector instrument with the holes on the overall device, one is assured of proper alignment of the device with the appropriate elements of the instrument, e.g., electrodes, optical detectors, thermal blocks, etc. In addition to alignment holes 218, the cover layer 200 also includes a beveled corner 220, which further ensures proper alignment of the device in the controller/detector instrument. Again, a number of different types of alignment structures may be used to accomplish this same purpose, including irregular edges, e.g., beveled, tabbed, etc., alignment pins, non-uniform shapes and the like.

As shown in FIG. 2A, the cover layer also includes convenience features. For example, textured regions 222 are provided on side-walls 216, to provide gripping surfaces for manual handling of the cover layer and assembled device. Also provided is registry port 224 disposed through the cover layer. Different numbers, sizes and/or shapes of registry ports are optionally provided in the cover layer to register the type of microfluidic device that has been inserted in a controller/detector instrument. This ensures that the proper interface is used, and/or the proper control program is being run.

Figure 3A:
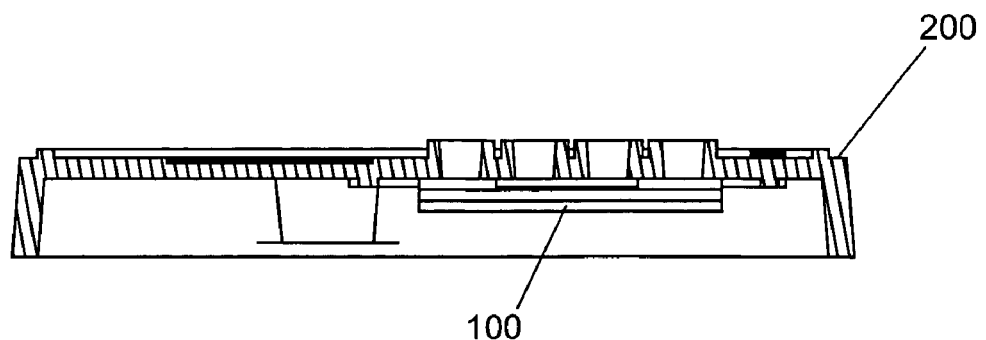
FIG. 3A illustrates a fully assembled microfluidic device that includes the layered body structure of FIG. 1 and the cover layer of FIG. 2 mated together.

FIG. 3A illustrates the fully assembled microfluidic device 300 including the body structure 100 mated with the lower surface of the cover layer 200, and bonded using, e.g., an adhesive, as described above. Rings are also optionally disposed between and surrounding the aligned apertures and ports of the cover layer and the body structure, as mentioned above. Furthermore, membranes are also optionally disposed between the aligned apertures and ports. The dimensions of planar devices, e.g., as shown in FIG. 3A, can vary substantially depending upon the application for which the device is to be used. Typically, however, the fully assembled devices have a rectangular shape and range from about 5 mm to about 200 mm on a side, and preferably are in the range of from about 10 mm to about 100 mm, and still more preferably, in the range of from about 20 mm to about 70 mm, e.g., about 50 mm on a side. For example, a square device approximately 50 mm on a side is shown. Such devices provide ease of handling as well as ready access to equipment already sized for handling substrates of this size, i.e., photographic slides.

Figure 3B:
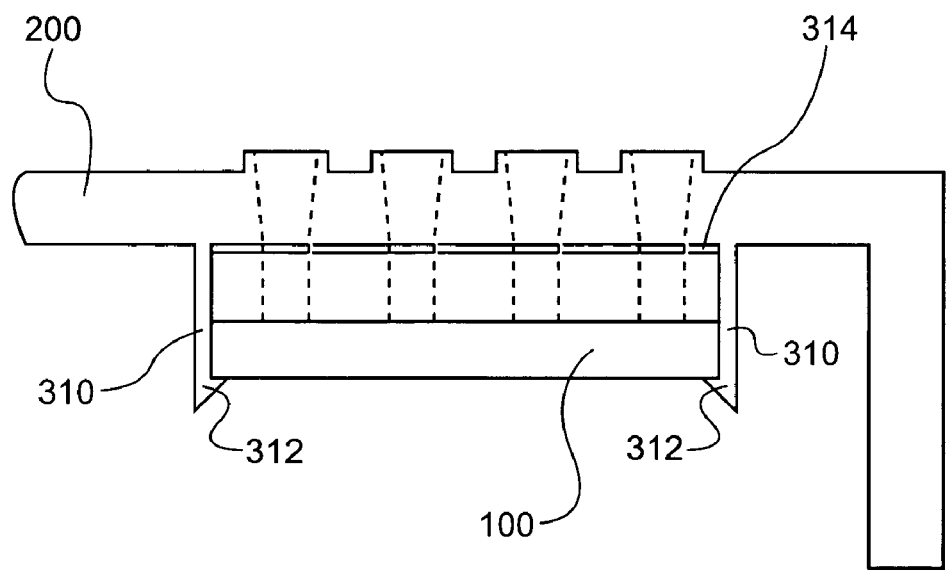
FIG. 3B illustrates an alternate mechanism for joining the body structure to the cover layer in the fully assembled device.

FIG. 3B illustrates a clamping mechanism integrated into the cover layer of the device. In particular, as shown, the cover layer 200 (partially shown), includes on its bottom surface, clip tabs 310. These clips flex to allow insertion of the body structure 100, then snap into place to lock the body structure 100 in position against the cover layer 200 with barbs 312. Gasket 314 provides a seal between the two structures, as well as providing the necessary flexibility to permit the clips to compressively clamp the body structure against the cover layer. The gasket 314 is optionally fabricated from a flexible material, such as latex, silicone, or the like, or a semi-rigid material, such as polytetrafluoroethylene (Teflon™), polypropylene, etc. The gaskets also optionally include the rings, discussed above, as integral components therein.

Although illustrated as a planar cover layer attached to a planar body structure, it will be appreciated that an appropriate cover layer is optionally joined to a non-planar microfluidic system, e.g., a tubular capillary or the like. In such cases, apertures in the cover layer are again fabricated to align with the ports, e.g., inlets and outlets of the capillary channel.

In addition to the above-noted advantages, e.g., isolation of reservoirs, increased reservoir volume, etc., the cover layers described for use in conjunction with the present invention also optionally include other useful features. For example, the shape of the aperture in the cover layer is optionally configured to receive a complementary structure on a filling apparatus, e.g., syringe or pump. Specifically, in some cases it is desirable to use a positive pressure source to assist in filling the channel networks of a microfluidic device with fluid. This is typically useful where the filling solution, e.g., running buffer, separation matrix, etc., is slower at wicking into the channel network via capillary action, due to viscosity effects. In operation, the running buffer, separation matrix, etc. is placed into one reservoir of the microfluidic device. A positive pressure is then applied to that reservoir thereby forcing the fluid throughout the channel network.

Figure 2F:
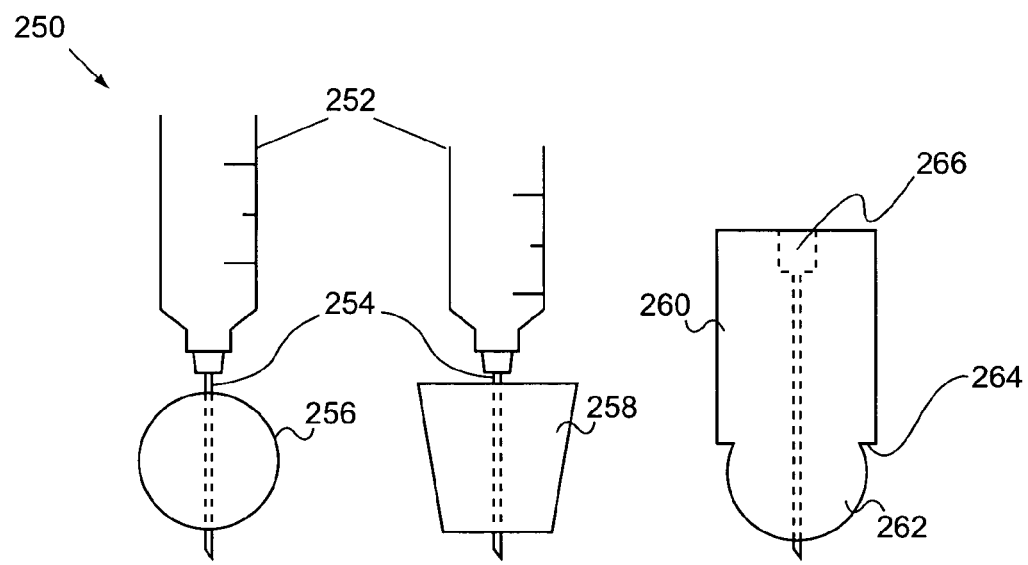
FIG. 2F illustrates the interaction of a filling device with the microfluidic devices of the invention.
Figure 2F:
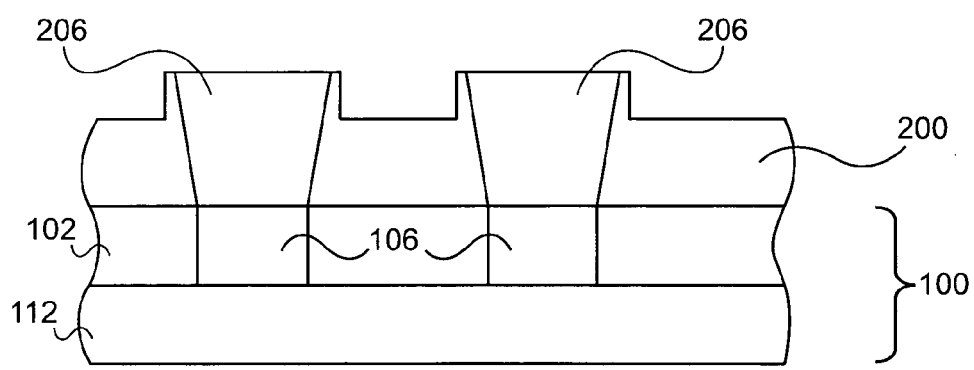

Application of the positive pressure is preferably carried out using an apparatus that sealably fits over the reservoir while not actually contacting the fluid contained therein. Examples of such devices, as well as appropriately configured apertures on the cover layer, are illustrated in FIG. 2F. As shown, the filling device 250 includes a syringe 252 and a rigid tube 254, e.g., a needle. The rigid tube/needle is inserted through a rubber, e.g., silicone, latex, etc., ball stopper 256 that is selected to properly fit within the aperture 206 in the cover layer 200. The conical shape of aperture 206 permits the ball stopper 256 to be inserted into the aperture 206. Compression of the stopper against the walls of the aperture then creates a positive seal. The rigid tube/needle 254 is further positioned within the ball stopper 256 so as to be able to apply pressure to the reservoir 106, without contacting the fluid within the reservoir 106. In particular, the tube is inserted through the stopper such that little or no tube length extends beyond the surface of the stopper, e.g., less than 2 mm, preferably less than 1 mm and more preferably less than 0.5 mm of the tube extending beyond the surface of the stopper.

Application of pressure by activation of syringe 252, then forces fluid within reservoir 106 into the channel network (not shown) of the device 100. Alternatively shaped stoppers 258 and 260 are also shown for use in the filling device. In the preferred stopper 260, the ball portion 262 of the stopper inserts into the aperture, and compression of the ball portion provides a positive seal. The ball shape allows one to insert the filling device at an angle of up to approximately 15° from normal to the plane of the cover layer 200, without adversely effecting the sealing ability of the filling device. Alternatively, the ball can be inserted until the flat ledge 264 contacts the upper surface of the cover surrounding the aperture 106. This provides a secondary seal for the filling device, in addition to the ball stopper. Although illustrated as a syringe, it will be appreciated that virtually any source of pressure is suitable for use in the filling device, including external pumps, pipettors and the like. The stopper optionally includes a recessed region 266 at the top for receiving the syringe 252 or pump outlet.

Additional functions are also optionally performed by the cover layer. For example, in some cases, it may be desirable to perform a separation function, e.g., a filtration, cell separation, molecular weight separation, affinity, charge-based or hydrophobic interaction type separations, on a sample that is to be introduced into the microfluidic device. Accordingly, an appropriate filtration or separation medium or membrane is optionally provided within or across the aperture on the cover layer. When the cover layer is mated to the body structure of the device, introduction of a sample into the body structure requires passage through the filter or membrane, and separation of particulate components, high molecular weight materials, and the like.

In further aspects, the cover layer performs a fluid handling and direction function, e.g., a manifolding function, where an aperture in the cover layer communicates with more than one reservoir on the body structure of the device, e.g., 2, 3, 4, 5, 10 or even 20 different reservoirs. Such a system is particularly useful where a single sample is to be subject to multiple different analyses within the body structure of the microfluidic device, e.g., in diagnostic applications where a single patient sample may be subject to multiple diagnostic tests. A variety of other modifications will be apparent to one of ordinary skill in the art, and are generally encompassed by the present invention, as set forth in the appended claims.

Alternatively, the cover layer may include other components useful in the operation of the microfluidic device and system, including e.g., integrated optical elements, e.g., lenses, gratings, coatings, polished detection windows, etc., as described in commonly owned U.S. patent application Ser. No. 09/030,535, entitled "Microfluidic Devices and Systems Incorporating Integrated Optical Elements," filed Feb. 24, 1998, which is incorporated herein by reference, in its entirety for all purposes. Such elements supplement or replace optical elements from an external detection system.

V. System Description

As alluded to above, the microfluidic devices described herein, are generally operated in conjunction with a controller instrument. Typical controller instruments include material transport systems, for affecting material, e.g., fluid, movement within and among the channels and chambers of a microfluidic device. For example, in the case of microfluidic systems employing pressure based fluid flow or that incorporate pressure actuated micropumps and valves, the controller instrument typically includes pressure sources as well as appropriate manifolds for delivering the appropriate pressures to complementary ports on the microfluidic device. The instrument then applies pressure/vacuum to activate the pumps and valves, or directly to fluids, to move those fluids through the channels of the device in a controlled fashion. In the case of microfluidic systems employing electrokinetic material transport systems, the controller typically includes an electrical power supply that is capable of delivering voltage gradients across the length of channels within the microfluidic device, as described above, when the device is mounted in the controller. Examples of particularly preferred power supplies are described in, e.g., Published International Application No. WO 98/00707, which is incorporated herein by reference in its entirety for all purposes.

As such, the controller typically includes an appropriate interface for delivering the voltage gradients to the channels of the device. Such interfaces are generally described in detail in commonly owned U.S. patent application Ser. No. 08/919,707, filed Oct. 9, 1997, and incorporated herein by reference for all purposes. In brief, such interfaces typically include a number of electrodes, operably coupled to electrical leads from the power supply. The controller also typically includes a nesting region, e.g., a well or platform, upon which the microfluidic device is mounted. The electrodes are positioned so as to be placed into electrical contact with the channels of the device. In preferred aspects, this is accomplished by providing a "clam shell" lid hinged to the nesting region so as to close over the top of the device. The device, e.g., as shown in FIGS. 1-3, is mounted on the nesting region with the reservoirs facing upward. The electrodes protruding from the lower surface of the clam-shell lid then insert into the reservoirs on the upper surface of the microfluidic device when the clam-shell lid is closed, so as to be placed into electrical contact with fluids in those reservoirs.

Environmental control elements are optionally included in the controller instrument, e.g., for maintaining the environmental conditions to which the microfluidic device is exposed, at optimal levels. For example, the controller optionally includes a thermal control element, e.g., a heating block, peltier device, etc.

In addition to including control elements, in preferred aspects, the controller instrument also includes a detection system for detecting the results of an operation performed in the microfluidic device. As such, the instrument is also referred to as a controller/detector instrument.

Examples of particularly preferred detection systems include fluorescent detection systems. Typically, these detection systems include a light source, such as a laser, laser diode, LED or high intensity lamp, within the controller/detector instrument. The detection system also typically includes appropriate optics, e.g., lenses, beam splitters, filters, dichroics, and the like, for directing the light source at the detection window of a microfluidic device mounted on the controller/detector. The optics also gather emitted fluorescence emanating from the channel(s) of the device, separate out reflected excitation light, and detect the emitted fluorescence, e.g., using a photodiode or photomultiplier tube (PMT). Other optical detection systems are optionally included within the controller/detector instrument, e.g., absorbance or colorimetric detection systems, and the like. Both fluorescence based and absorbance based detection systems are well known in the art.

The controller/detector instrument is also typically interfaced with an appropriate processor, e.g., an appropriately programmed computer, which instructs the operation of the material transport system, e.g., applied voltages, timing, etc. The processor also typically is operably linked to the detection system of the controller/detector instrument, so that the computer can receive, store and manipulate the data collected from the detection system.

VI. Example

A. Use of Membranes in Microfluidic Devices

A piece of nylon mesh membrane (40 μm pore size) was placed on the first surface of a DNA 7500 LabChip™ cover layer. Thereafter, an ns88 chip was oriented on the cover layer and UV curing DYMAX™ adhesive was applied using standard manufacturing techniques. The adhesive wicked under the chip and through the membrane, but did not encroach upon the membrane disposed in the wells of the device. After the adhesive was cured, 5 μl of buffer were placed on the membrane in one of the wells. The buffer successfully passed through the membrane and filled the microchannels of the chip.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A microfluidic device, comprising:
    a body structure comprising at least a first microscale channel network disposed therein, the body structure having a plurality of ports disposed in the body structure in fluid communication with the first microscale channel network; and,
    a cover layer comprising a plurality of apertures disposed through the cover layer and at least first and second annular rings arranged circumferentially around each of the apertures and extending downwardly from a lower surface of the cover layer, the cover layer being mated with the body structure whereby each of the apertures is aligned with at least one of the plurality of ports.

2. The microfluidic device of claim 1, further comprising an annular groove which extends circumferentially around each of the plurality of apertures of the cover layer and is disposed between the first and second annular rings.

3. The microfluidic device of claim 1, wherein the first and second annular rings have a width of between about 0.4 and 0.5 mm.

4. The microfluidic device of claim 2, wherein each of the annular grooves have a width of between about 0.2 and 0.8 mm.

5. The microfluidic device of claim 1, wherein the first and second annular rings have a width of between about 0.2 and 0.7 mm.

6. The microfluidic device of claim 1, wherein each of the annular grooves have a depth of between about 0.3 and 0.5 mm.

7. The microfluidic device of claim 1, wherein the cover layer is bonded to the body structure with an adhesive.

8. The microfluidic device of claim 7, wherein the adhesive is a UV curable adhesive.

9. The microfluidic device of claim 1, wherein the cover layer is an injection molded polymeric part.

10. The microfluidic device of claim 1, wherein the cover layer is a cast polymer part.

11. The microfluidic device of claim 1, wherein the body structure comprises first and second planar substrates which comprise silica based substrates.

12. The microfluidic device of claim 11, wherein the silica based substrates are made from glass.

13. The microfluidic device of claim 1, wherein the body structure comprises first and second substrates made from a polymeric material.

14. The microfluidic device of claim 13, wherein the polymeric substrate is selected from polymethylmethacrylate (PMMA), polycarbonate, polytetrafluoroethylene, polyvinylchloride (PVC), polycycloolefin, polydimethylsiloxane (PDMS), polysulfone, polystyrene, polymethylpentene, polypropylene, polyethylene, polyvinylidine fluoride and ABS.

* * * * *